(12) United States Patent
Hodgetts et al.

(10) Patent No.: US 7,704,467 B2
(45) Date of Patent: Apr. 27, 2010

(54) WEEKLY FLOATER POOL SANITIZER

(75) Inventors: Peter Kenneth Hodgetts, Gauteng (ZA); Richard M. Mullins, Cape Coral, FL (US)

(73) Assignee: Arch Chemicals, Inc., Norwalk, CT (US)

( * ) Notice: Subject to any disclaimer, the term of this patent is extended or adjusted under 35 U.S.C. 154(b) by 654 days.

(21) Appl. No.: 11/314,693

(22) Filed: Dec. 20, 2005

(65) Prior Publication Data

US 2006/0276338 A1 Dec. 7, 2006

(30) Foreign Application Priority Data

Dec. 23, 2004 (ZA) .............................. 2004/10370

(51) Int. Cl.
*B01D 11/00* (2006.01)
(52) U.S. Cl. ...................................... 422/265; 137/268
(58) Field of Classification Search ................ 422/265, 422/274, 276, 277, 99, 104; 210/167.1, 167.11, 210/167.19, 167.2; 137/268
See application file for complete search history.

(56) References Cited

U.S. PATENT DOCUMENTS

| | | | | |
|---|---|---|---|---|
| 2,874,032 A | * | 2/1959 | Kuehner | ..................... 422/274 |
| 3,607,103 A | * | 9/1971 | Kiefer | ......................... 422/119 |
| 4,217,331 A | | 8/1980 | Schaub | |
| 4,763,685 A | * | 8/1988 | King, Sr. | ..................... 137/268 |
| 5,164,109 A | | 11/1992 | Wojtowicz | |
| 5,614,102 A | | 3/1997 | Sakurada | |
| 6,065,690 A | | 5/2000 | O'Brien | |
| 6,093,422 A | | 7/2000 | Denkewicz, Jr. et al. | |
| 6,503,467 B1 | * | 1/2003 | Robinson et al. | ............ 422/265 |
| 2004/0175311 A1 | | 9/2004 | Cormier | |

* cited by examiner

*Primary Examiner*—Jill Warden
*Assistant Examiner*—Cedric Chan
(74) *Attorney, Agent, or Firm*—Wiggin and Dana LLP

(57) ABSTRACT

A composition for the treatment of a liquid, particularly a body of water, such as a swimming pool, spa, or the like. The composition includes calcium hypochlorite, a water soluble zinc salt for controlling algae, and sodium aluminate as an agglomerating agent that may safely be combined with said calcium hypochlorite and said zinc salt. A floating chemical dispenser for containing and dispensing chemicals to treat a body of water. The dispenser includes an upper end float, a container adapted to contain chemicals, the container removably joined with the upper end float, and a free end float joined with the container. The free end float is configured so that a central axis of the container and upper end float is not substantially orthogonal to a surface of the water.

5 Claims, 3 Drawing Sheets

US 7,704,467 B2

WEEKLY FLOATER POOL SANITIZER

BACKGROUND OF THE INVENTION

1. Field of the Invention

This invention relates to a composition for the treatment of a liquid, particularly a body of water, such as a swimming pool, spa or the like. The invention provides for the controlled release of the components of the composition for continuous and effective sanitisation and algae control to such a body of water.

2. Brief Description of Art

Compositions for the sanitization and algae control of bodies of water, such as swimming pools, spas and the like, are well known. It is particularly well known for one of the components of the composition to be calcium hypochlorite. Further, U.S. Pat. No. 5,164,109 to Wojtowicz, which is incorporated herein in its entirety by reference, describes a composition consisting essentially of calcium hypochlorite and a water soluble zinc salt. The US patent teaches that the control of algae is enhanced by use of such a composition and that the combination of these components tends to avoid a common problem, which is encountered in the use of other compounds, namely the reduction in the amount of available chlorine available for sanitization.

It would be a further advantage to provide a compound, such as that described above, having enhanced algicidal properties and which, in addition contains a agglomerating agent to facilitate the removal of suspended solids from the body of water and to thereby reduce biological load in the body of water (in this specification, an agglomerating agent is to be given a wide meaning and includes coagulating agents and flocculating agents). However, calcium hypochlorite is notoriously averse to combination with many other chemical compositions and the safety of the public must always be borne in mind in combining calcium hypochlorite with, or even housing calcium hypochlorite in proximity to, any other chemical components. Accordingly, there is a need for a chemical composition, which includes a sanitizer in the form of calcium hypochlorite (in anhydrous or hydrated form) together with an algicide comprising a soluble zinc salt (which may be either an inorganic or organic salt), and an agglomerating agent which may be safely combined therewith for storage, transport, sale and use in the treatment of a body of water.

BRIEF SUMMARY OF THE INVENTION

One aspect of the invention is a composition for the treatment of a liquid, which includes the following: calcium hypochlorite; a water soluble zinc salt for controlling algae; and an agglomerating agent that may safely be combined with the calcium hypochlorite and the zinc salt.

Another aspect of the invention is a floating chemical dispenser for containing and dispensing chemicals to treat a body of water. The dispenser includes an upper end float, a container adapted to contain chemicals, and a free end float. The container includes a first wall at one end and a bottom wall at a second end with side walls therebetween. The side walls include a plurality of openings adapted to dispense chemicals. The first wall is removably joined with the upper end float. The container and upper end float have a central axis when joined together. The central axis defines a first center of flotation for the upper end float and the container. The free end float is joined with the bottom wall within the container. The free end float has a second center of flotation. The free end float is positioned so that the second center of flotation is off-center from the first center of flotation. The free end float is configured so that the central axis is not substantially orthogonal to a surface of the water when the dispenser is floating in the water.

Yet another aspect of the invention is a method of treating a body of water, which includes the following steps: providing a floatable chemical dispenser having closable openings; inserting a composition including calcium hypochlorite, a water soluble zinc salt for controlling algae, and sodium aluminate as an agglomerating agent that may safely be combined with the calcium hypochlorite and said zinc salt into the dispenser; opening the openings of the dispenser; and floating the chemical dispenser in the body of water.

DETAILED DESCRIPTION OF THE DRAWINGS

The invention is now described, by way of example, with reference to the accompanying diagrammatic drawings in which:

FIG. 1 shows a sectional side view of a dispensing device, in accordance with the invention, for treating a body of water, such as a swimming pool, spa or the like;

DETAILED DESCRIPTION OF THE INVENTION WITH REFERENCE TO THE DRAWINGS

Figure 1:
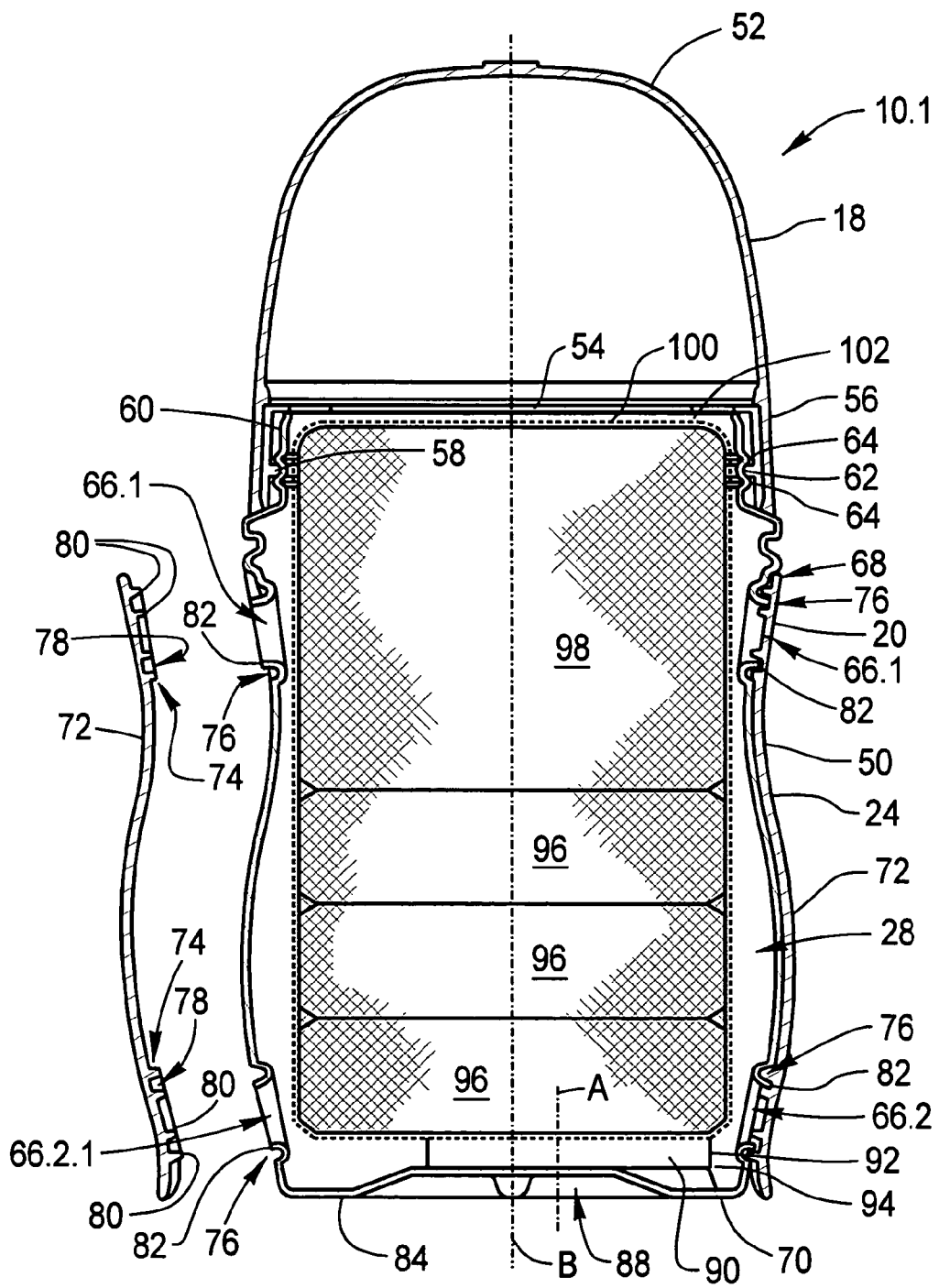

In FIG. 1 reference numeral 10.1 generally refers to a chemical dispenser in accordance with the invention. The chemical dispenser 10.1 is adapted to float in the body of water to be treated and to dispense chemicals from a container of the device, the container containing a composition comprising calcium hypochlorite, a water soluble zinc salt, and an agglomerating agent, preferably sodium aluminate, i.e. the composition of the invention.

The dispenser 10.1 has a generally circular profile and a smoothly curved waist 50 and rounded upper end 52, comprising a float 18. The float 18 is hollow and is sealed by means of a wall 54 which serves to separate the float 18 from the container 20. The float 18 has an annular skirt 56 with an inwardly projecting locating ridge 58 defined thereon. A neck 60 of the container 20 has an outer locating annular channel 62 defined between a pair of spaced annular channel walls 64. The ridge 58 of the skirt 56 and the channel 62 of the container 20 co-operate in a click-fit fashion to provide for the non-releasable attachment of the float 18 to the container 20 at the time of filling of the container 20, after insertion of the chemical composition. Further, two pairs of circular openings 66 are defined in the walls 24 of the container 20 on diametrically opposed sides thereof. Each pair of openings 66 comprises an upper opening 66.1 in an upper region 68 of the container 20 and a lower opening 66.2 proximate the free end 70 of the container 20. A pair of closing strips 72 is provided, each of which has a pair of engaging formations 74 to engage with complimentary engaging formations 76 arranged at the openings 66 of the container 20, thereby to provide a removable closure for each of the openings 66. The engaging formations 74 of the closing strips 72 comprise annular channels 78 defined between spaced annular ridges 80 defined on the strips 72 to be in register with and engage in a click-fit manner with outwardly projecting annular lips 82 around the respective openings 66 of the container 20.

The container 20 has a bottom wall 84 at its free end 70 having a central inward depression 88 defined thereon. A disk 90 of expanded polystyrene 92 provides a float 94 and is adhesively attached to the bottom wall 84 of the container 20 on its inside. The disk 90 is positioned off-center, so that its center of flotation indicated on the line A, is spaced from the central axis indicated at B, of the container 20 and is on a diametrically opposed side of the center of the bottom wall 84 of the container 20 from one of the lower openings 66.2.1. It will thus be appreciated that the float 94 will provide a moment about the center of flotation of the dispenser which lies on the line B (without the float 94) and will cause the container 20 to tilt when in equilibrium in calm water, so that the central axis B of the container 20 is no longer orthogonal with the surface of the water, as would tend to be the case without the float 94. As the container 20 tilts, the lower opening 66.2.1 will be displaced to a position near the lowest point on the container 20, thereby facilitating drainage from the container 20 under gravity. It will be appreciated that, in use, as the contents of the container 20 are progressively dissolved, the center of flotation of the entire dispenser 10.1 will gradually move and the dispenser will tend to float with the container 20 at a greater and greater angle to vertical, thereby providing an indication that the contents of the container 20 are exhausted.

The container 20 includes a chamber 28, which contains four chemical tablets, three of which 96 are composed of compressed calcium hypochlorite and the larger of which 98 contains a compressed composition comprising calcium hypochlorite, an algicide and an agglomerating agent, being respectively zinc sulfate and sodium aluminate. It will be appreciated that the various chemicals of the composition may be provided in any suitable format, such as pellets, granules or the like. The form of the various chemicals may be selected to provide for their dissolution at a preferred rate.

The tablets 96, 98 are enshrouded in a mesh bag 100 of a plastics material 102, the mesh size of which is determined with a view to permitting relatively unimpeded contact of the tablets 96, 98 with the surrounding water flowing into the container 20, while entrapping particulates of a preselected size, comprising undissolved solids from the chemicals. Clearly, the mesh 100 will not prevent all undissolved solids from exiting the container 20 into the surrounding body of water, but unsightly larger particles may be retained in the container 20 to be discarded once the container 20 is exhausted.

Figure 2:
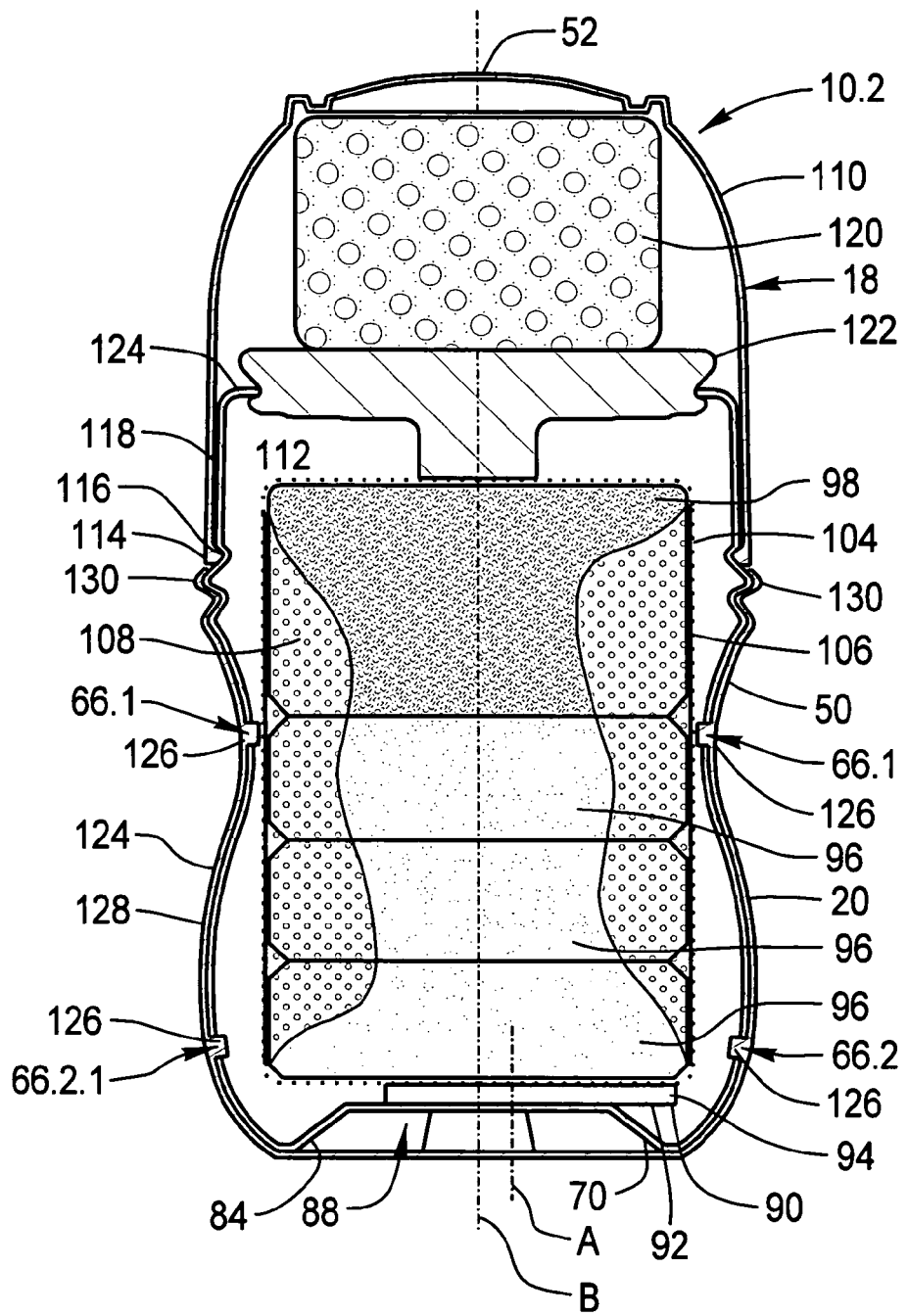
FIG. 2 shows a sectional side view of a further embodiment of the dispensing device.

In FIG. 2 a further embodiment 10.2 of the dispenser is shown and, with reference to FIG. 1, like numerals indicate like components unless otherwise stated. The dispenser 10.2 operates as described in respect of the dispenser 10.1 of FIG. 1, particularly insofar as the orientation of the container 20 of the dispenser 10.2, in use. However, in the dispenser 10.2 the chemicals 96 and 98 are contained within a perforated bag 104 of a plastics material 106. The chemicals 96 and 98 are sealed within the bag 104, but may merely be enshrouded therein. The bag 104 has regularly spaced perforations 108 which are preferably between 10 and 100 μm in diameter. In the most preferred embodiments of the invention, the perforations 108 are between 30 and 60 μm in diameter.

The container 20 of the dispenser 10.2 is once again of circular cross-section, having a narrowing, smoothly curved waist 50. Further, a cap 110 is non-releasably attached to the container 20 by means of an inwardly projecting annular ridge 112 defined on the cap 110 at its open end 114. The ridge 112 co-operates with an annular channel 116 defined on a side wall 118 of the container 20. The cap 110 is fitted in a snap-fit manner to the container 20 at the filling point of the dispenser 10.2 after filling the container 20. Otherwise than with the dispenser 10.1, there is no wall separating the container 20 and the cap 110. A polystyrene block 120 is received within the cap 110, the polystyrene block 120 and the cap 110 together providing a float 18 for the dispenser 10.2. A spacer 122 is secured to the container 20 at its open end 124. The spacer 122 acts as a stop against which the chemicals 96, 98 abut during storage and transport and also serves to support the polystyrene block 120 during storage and transport. As with the dispenser 10.1, the container 20 of the dispenser 10.2 has two pairs of opposed openings 66 defined in its side wall 118, each pair of openings 66 comprising an upper and lower opening, 66.1 and 66.2 respectively. A closure for the openings 66 is provided by a generally U-shaped clip 124 having pairs of inwardly extending lugs 126 which are received in, and act as stoppers for, the openings 66 of the container 20. The clip 124 is of a resiliently flexible plastics material 128 and, once clipped in place, is removed by urging ends 130 of the clip 124 apart and removing the entire one-piece clip 124 from the container 20, thereby exposing the openings 66 for use. The chemical 98 comprises a combination of compressed calcium hypochlorite, zinc sulfate and sodium aluminate compressed into relatively small pellets having a relatively large surface area in relation to their volume, resulting in their dissolving rapidly in contact with water. The different chemicals of the composition 98 may be mixed before compression into pellets or the separate chemical components may be palletized before mixing in desired proportions. The remaining tablets 96 of calcium hypochlorite dissolve at a relatively slower rate.

The chemical composition 98 contains calcium hypochlorite in the range of 40 to about 95 percent by weight of calcium hypochlorite. The calcium hypochlorite is in an amount to achieve a dosage of 0.1 to 10 parts per million. The zinc sulfate is in an amount to provide the water with a concentration of zinc from about 2 to about 6 parts per million. The sodium aluminate is provided in an amount to achieve a dosage rate between about 0.01 to 10 parts per million of water, but preferably does not exceed 2 parts per million. For the dispensers 10.1 and 10.2 of FIGS. 1 and 2, these dosages are calculated on the basis of an average sized household swimming pool of about 50 000 litres, taking into account the average rate of dissolving of the algicide and coagulant in water passing through the dispenser. In these circumstances, it has been found that about 340 g of 68% calcium hypochlorite, 7.5 g of zinc sulphate and 50 g or sodium aluminate in the composition 98 is effective. The tablets 96 contain about 600 g of calcium hypochlorite of 68% concentration, sufficing to treat the swimming pool for about one week. It will, of course, be appreciated that the ratios of the components of the composition and their actual weights may be selected to provide dosing at required rates and concentrations. The chemicals in the composition 98 dissolve rapidly in water and are dispensed within a matter of hours, whereas the tablets 96 dissolve slowly over the desired treatment period.

COMPATIBILITY TEST

A test was conducted to investigate the compatibility of a system of solid chemicals used to enhance the clarity of pool water. They system is described below:

1. Calcium hypochlorite, $Ca(OCl)_2$, [7778-54-3],
2. Zinc sulfate monohydrate, $ZnSO_4.H_2O$, [7446-19-7]
3. Sodium aluminate, $No_2O.Al_2O_3.3H_2O$, [1302-42-7]

The normal and most severe conditions used to investigate the compatibility of the system mentioned included:—

Temperature: ambient

Thermal conditions: adiabatic

Impurities: (i) dry (i.e. no water), (ii) with water

The mass of water added in the experiment was approximately 10% of the mass of the final mixture. This mass was chosen arbitrarily so as not to swamp any reaction, but to be present in sufficient quantities to create noticeable reactions. No attempt was made to investigate the effect of varying the quantity of water on observed reactions as this was beyond the scope of the task.

The onset of chemical reaction was monitored by observing temperature changes under adiabatic conditions using a 250 ml insulated vessel with paper plug. These adiabatic conditions simulated much larger vessels with limited cooling due to a small surface area to volume ratio. Mixing with a wooden rod did introduce energy into the system. Temperature was measured using a −10 to 50° C. thermometer graduated in 2° C. steps. Sample mass was also monitored as an indicator of reaction using a calibrated balance capable of measuring 1 g.

Two mixtures of sulphates were prepared by adding weighed amounts of the following components to the vessel with extended stirring:

| Mixture 1 | Mixture 2 |
| --- | --- |
| 1) 10 g of zinc sulfate monohydrate | 3) 5 g of zinc sulfate monohydrate |
| 2) 10 g of sodium aluminate | 4) 5 g of sodium aluminate |

Thereafter, 80 g (for mixture 1) or 90 g (for mixture 2) of calcium hypochlorite was added to the vessel with stirring. The initial temperature of both mixtures was 27° C. After more than five minutes of stirring the temperature of both mixtures remained at 27° C. The mixtures were allowed to stand for a further 10 minutes and no temperature changes were observed. The mass of the mixture did not change during this period.

At this point 10 g of tap water was added to each of the mixtures in the vessel with stirring. The temperature of the water was 25° C. Vigorous bubbling was observed and the temperature rose rapidly to a maximum of 50° C. After about 1.5 hours, the mass was recorded indicating a loss of 2 g from each mixture. The liberation of a gas, presumably chlorine, was observed after the addition of the water.

Figure 3:
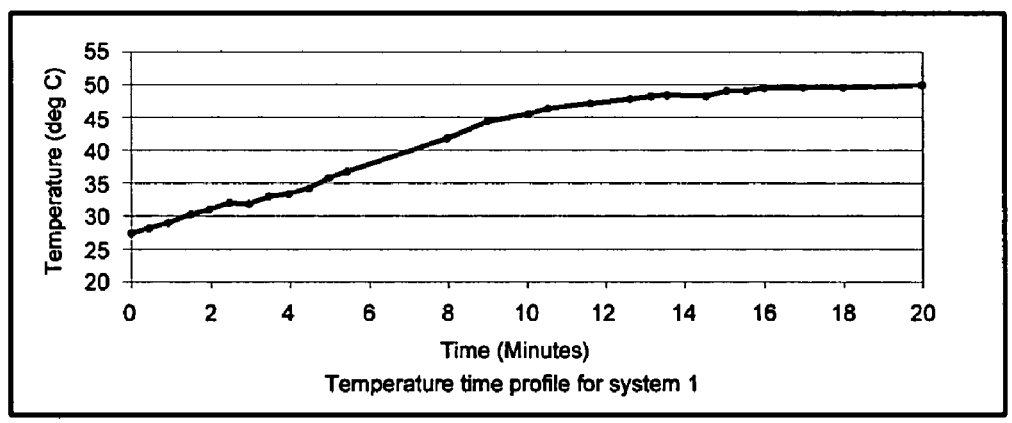
FIG. 3 shows results of testing of a composition in accordance with the invention.

The temperature time profile recorded during the addition of water to mixture 1 is shown in FIG. 3.

The maximum rate of temperature rise was 3° C./min measured at the 9 minute mark.

Clearly, some chemical reaction occurred on the addition of water and it was probably the release of chlorine, the desired action of calcium hypochlorite. No significant interactions were observed in any of the systems in the dry state. However, under the experimental conditions described above, an exothermic reaction occurred in the presence of water, probably liberating chlorine.

It should be understood that any of the features, characteristics, alternatives, or modifications described regarding a particular embodiment herein may also be applied, used, or incorporated with any other embodiment described herein.

A number of embodiments have been described. Nevertheless, it will be understood that various modifications may be made without departing from the spirit and scope of the invention. Accordingly, other embodiments are within the scope of the following claims.

What is claimed is:

1. A floating chemical dispenser for containing and dispensing chemicals to treat a body of water, said dispenser comprising:
    an upper end float;
    a container adapted to contain chemicals, said container having a first wall at one end and a bottom wall at a second end with side walls therebetween, said side walls including a plurality of openings adapted to dispense chemicals, said first wall removably joined with said upper end float, said container and said upper end float when joined together having a longitudinal central axis of symmetry, said central axis defining a first center of flotation for said upper end float and said container, said central axis intersecting said bottom wall; and
    a free end float joined with said bottom wall along an interior surface thereof within said container, said free end float having a diameter less than that of said bottom wall, said free end float having a second center of flotation, said free end float being positioned off-center with respect to said central axis so that said second center of flotation is off-center from said first center of flotation, wherein said free end float is configured so that said central axis is not substantially orthogonal to a surface of the water when the dispenser is floating in the water.

2. A dispenser according to claim 1, wherein said container defines a chamber for containing the chemicals.

3. A dispenser according to claim 2, further comprising a mesh bag for containing the chemicals within said chamber.

4. A dispenser according to claim 1, further comprising closing strips that removably attach to said container thereby covering said plurality of openings.

5. A dispenser according to claim 1, further comprising a generally u-shaped clip that removably attaches to said container thereby covering said plurality of openings.

* * * * *